United States Patent [19]

Haggar, deceased et al.

[11] 4,328,912
[45] May 11, 1982

[54] SELF-CONTAINED VALVED PACKAGE

[76] Inventors: Theodore Haggar, deceased, late of Totowa, N.J.; by Phyllis Haggar, administratrix, 5 Artillery Park Rd., Totowa, N.J. 07512

[21] Appl. No.: 919,316

[22] Filed: Jun. 26, 1978

[51] Int. Cl.³ .......................................... B05B 11/04
[52] U.S. Cl. .................................................. 222/212
[58] Field of Search .............. 222/212, 491, 107, 494, 222/215, 512, 511

[56] References Cited

U.S. PATENT DOCUMENTS

| | | | |
|---|---|---|---|
| 2,663,461 | 12/1953 | Brown | 222/107 |
| 3,610,477 | 7/1969 | Herzig | 222/213 |
| 3,635,376 | 1/1972 | Hellstrom | 222/107 |
| 3,815,794 | 6/1974 | Carlisle | 222/491 |

Primary Examiner—Stanley H. Tollberg

[57] ABSTRACT

A dispensing package for a fluent commodity comprising a container with a self-contained depression/impression valve in the wall of said container operable between an open position and a closed position for discharging the fluent commodity.

Further, the invention is of a dispensing package for a fluent commodity having a container with walls of a semirigid material; an elongated discharge passage attached thereto having two opposed substantially flat wall portions; a depression in the first one of the wall portions operable between a smooth-curved position and a multiply curved position; and an impression in the second one of the wall portions which, when the depression is in the smooth-curved position, mates with and seals against the depression for preventing discharge of the fluent commodity, and, which when the depression is in the multiply curved position provides for at least one opening between the two opposed wall portions, for permitting discharge of the fluent commodity.

12 Claims, 7 Drawing Figures

U.S. Patent  May 11, 1982  4,328,912
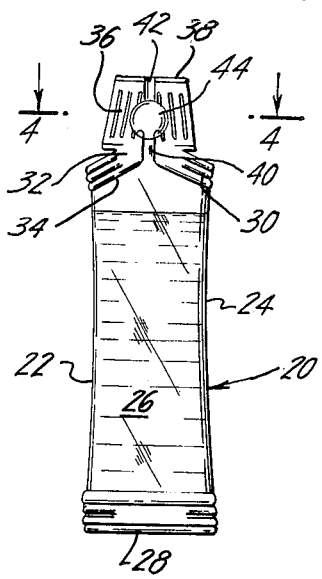
FIG.1
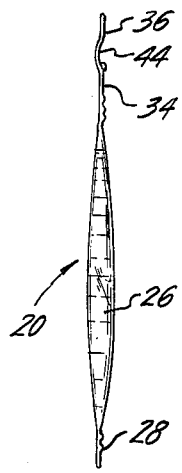
FIG.2
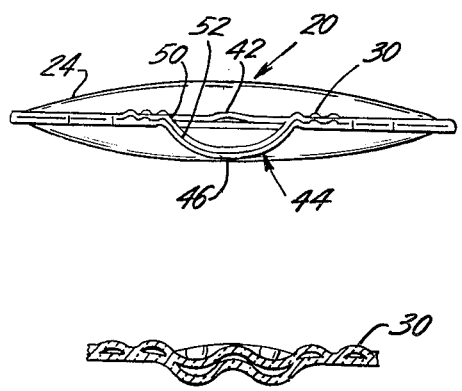
FIG.3
FIG.5
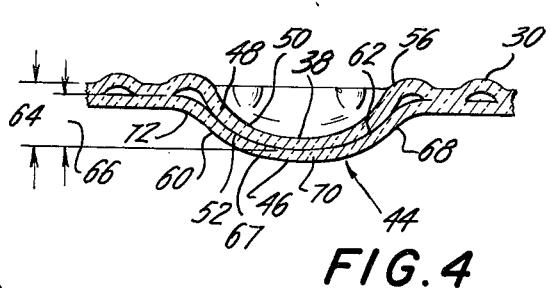
FIG.4
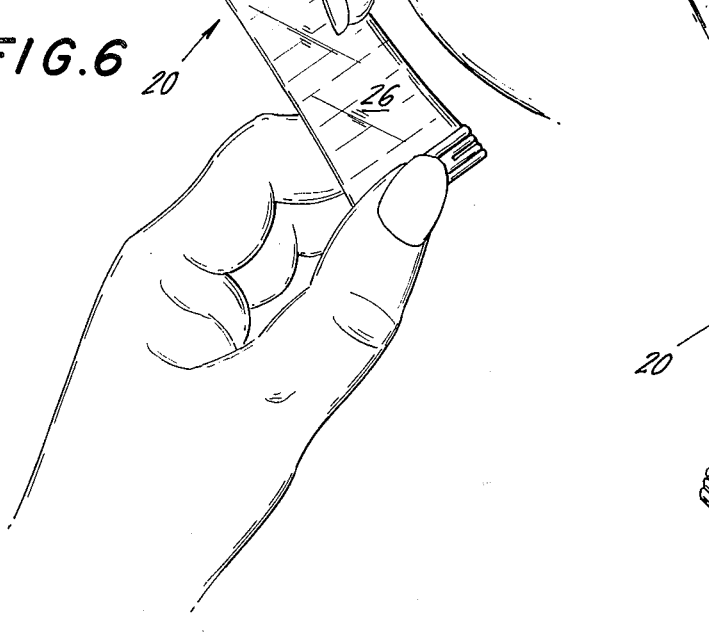
FIG.6
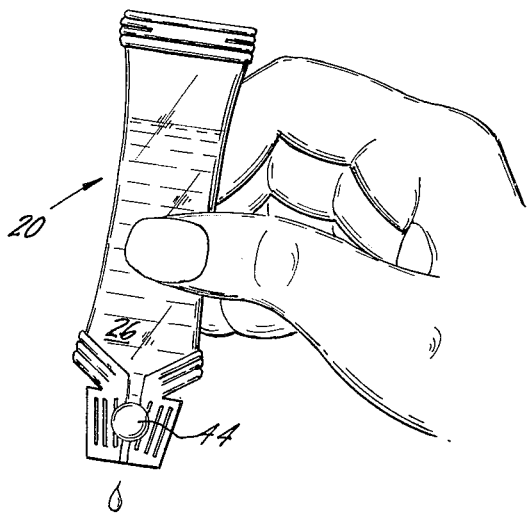
FIG.7

SELF-CONTAINED VALVED PACKAGE

BACKGROUND OF THE INVENTION

1. Field of the Invention

This invention relates to a self-contained valved package for a fluent commodity, and more particularly, a package with a depression/impression valve in the wall thereof. The invention is most immediately and widely applicable to the collapsible tube art and specifically to packages used for extremely small volumes of fluid.

2. Description of the Prior Art

Hundreds of products are packaged in small volume tubes or flat packages which most commonly are used a single time and as the package is not reuseable, the balance of the product and the package are discarded. Frequently, sample sizes of medicaments, such as, ophthalmic solutions and antibiotic ointments; dyes and pigments; inks; personal products, such as, hair preparations, lotions, creams, perfumes and colognes are packaged in small plastic or foil containers used once and discarded. Waste is inherently present, even encouraged, in such a sampling process.

The promotional value alone of reuseability at no substantial increase in package cost is inestimable.

In the past, various types of tubes and containers for these products have been placed in the market or proposed. While all the containers had discharge openings, most of these orifices are closed with removable cap members. Devices of this character, while having been widely used, have been subject to the difficulty of the loss of the removable cap making it difficult, if not impossible, thereafter to properly cover the discharge orifice. After the loss of the removable cap, certain commodities, notably glue, cement, and toothpaste, deteriorate or harden upon contact with the atmosphere. Such products often then become unusable and the remaining portion is discarded.

Other packages have been marketed having closures which are solely operated by pressure being exerted against the wall or walls of the package. Most popularly such closures include lip-like terminations that are closed when no pressure is exerted against the walls of the package. Such products often have the drawback that a small quantity of product lodges in the discharge termination and holds the lip portions thereof open to the atmosphere leading to the similar conditions as hereinbefore described. Further, with tubes with lip-like openings, accidental or inadvertent squeezing results in unwanted discharge of the product.

As the results of the patentability search described below indicate, a substantial array of dispensing packages and collapsible tube devices are at hand. However, when the prior art is examined with the package of this invention being understood both as to structure and operational aspects afforded by such structure, the disclosed invention appears novel and unobvious.

The search was conducted primarily in Class 222 in which most of the packaging art is classified, and also included Class 401, in which applicators combined with collapsing wall tubes are classified (Cl. 401/152 et seq.). Within Class 222, subclasses describing resilient wall devices, dispensing valve, wall actuation, flow control between fixed plates, miscellaneous outlet shapes and two-position tube tops were among those examined. The following pertinent patents were uncovered:

| U.S. Pat. No. | Inventor | Title |
| --- | --- | --- |
| 3,964,504 | Daubenberger et al | Check valve |
| 3,711,011 | Kugler | Resealable packaging device |
| 3,610,477 | Herzig | Automatic closure for containers |
| 3,184,121 | Volckening | Package with self-siding closure |
| 3,131,836 | Van Baarn | Closure for tubes and the like |
| 3,063,601 | Hertz | Self-sealing collapsible tubes |
| 3,012,698 | Wiederquist et al | Resilient dispensing tube |
| 2,546,709 | Abarr | Self-closing tube |
| 2,364,307 | Mossett | Closure for collapsible tubes |
| 2,309,895 | Griffith | Closure for collapsible tubes |

The structures shown in the prior art for packaging closure are either multiple part arrangements where a valve stem or a hinged cover is moved from obstructing flow or wall openings (reminiscent of the old glue bottles) in which a portion of the wall is stressed to provide flow. Of the latter group, the Abarr U.S. Pat. No. 2,546,709 shows a discharge orifice formed by a pair of lips 21 and 22 that are opened by applying pressure to point 13a.

The patent to Herzig, U.S. Pat. No. 3,610,477, is instructive in that it teaches the automatic closure for squeezeable containers comprising a neck having tapered side edges sealed together to form an openable outlet having opposed lips either one or both of which is advantageously provided with an inherent reentrant curve, bow or act so that these lips normally oppose and preferably bear against each other providing a closure, except when manual or the like pressure is applied to the contained material.

Of particular relevance in this are is the package with self-sealing closure patented by Volckening, U.S. Pat. No. 3,184,121, and assigned to Ivers-Lee Company. The patent describes a package of the type comprising at least two flexible layers or sheets of packaging material. Such packages include those formed from metal foil or laminated sheets of cellulose acetate and polyethylene, or suitable synthetic plastic material permanently sealed together in zones forming and bounding between the layers a commodity containing compartment having resilient self-sustaining walls with an elongated discharge passage openable between layers. The package has a discharge passage which shall be openable upon application of pressure exteriorly to the portions of the layers forming the walls of the compartment and shall be automatically closed upon release of such pressure.

Although of interest, none of the above patents reviewed on the prior art search showed the package of the invention, nor, when taken in combination, did the teachings make obvious the package of the invention.

SUMMARY OF THE INVENTION

It is the general object of this invention to avoid and overcome the foregoing and other difficulties of and objections to prior art practices by the provision of improved valved packages.

Essentially, in accordance with the present invention, a container for storing a fluent commodity is provided which includes a novel, self-contained valve that is simple and economical to manufacture and use. The valve is formed from two semirigid, flat walls having an outlet passageway in the mating surfaces thereof and medial the ends of the said passageways, there being interposed a depression in one of the walls and a corresponding impression in the other wall. Because of the nature of the material of construction, the depression of the one sheet is operable between a smooth-curved position which seals the passageway and a multiply-curved position which opens the passageway.

A further object of this invention is to provide a novel package which is unitary in design and easy to fill with the product.

A further object of the invention is to provide a package with a resealable valve.

A yet further object of this invention is to provide a package which utilizes a depression/impression valve and a method for making the same.

A still yet further object of this invention is to provide a package with a resealable valve outlet that is adapted to spray dispensing of the product.

A feature of the present invention is the ability to thoroughly mix the product by kneading the container prior to opening the discharge valve.

A feature of the present invention is the high reliability of the sealing mechanism together with a positive snap-to-seal action.

The aforesaid objects and features of this invention, and other objects and features which will become apparent as the description proceeds, are achieved by the self-contained valved package.

BRIEF DESCRIPTION OF THE DRAWINGS

The foregoing and other objects, features, and advantages of the invention will become apparent from the following description and claims, and form the accompanying drawings in which:

FIG. 1 is a front view of a self-contained valved package of the present invention for a fluent commodity showing the valve-to-package relationship;

FIG. 2 is a side view of the self-contained valved package of FIG. 1;

FIG. 3 is a plan view of the upper part of the valve portion of FIG. 1 in the smooth-curved position, showing in detail the depression formed therein, which depression acts both as the valve body and the valve gate; s-sectional view of the valve portion of FIG. 1 in the smooth-curved position, showing in detail the sealed package which is formed by the structure of FIGS. 3 and 4;

FIG. 6 is a cross-sectional view of the valve portion of FIG. 1 in the multiply-curved position showing in detail the resealable open package which is formed by the structure of FIGS. 3 and 4;

FIG. 7 is a cross-sectional view of the valved portion of FIG. 1 showing the use of the impression of FIG. 4 to operate the depression of FIG. 3 to the multiply-curved position;

FIG. 8 is an operational view of the package of FIG. 2 showing the application of pressure to the sidewall of the package to assist in discharging the fluent commodity through the open valve shown in FIG. 6.

DESCRIPTION OF THE PREFERRED EMBODIMENTS

With specific reference to the form of this invention illustrated in the drawings, and referring particularly to FIGS. 1 and 2, a dispensing package with a self-contained depression/impression valve is indicated generally by reference numeral 20.

For the purpose of this description a depression/impression valve is defined as a fluid flow control device for regulating the flow in a passageway at or near the common surface of two semirigid, abutting, flat members in one of which members there is formed a depression blocking the passageway; the depression extends through the common surface on a smooth arcuate curve (usually a spheric section) and on the other one of which members there is formed an impression in which the depression is sealingly seated; the two formed valve members are moveable so that the pressure on the convex aspect of the impression member can actuate the depression member to form a multiply curved state or position which provides for an opening of the passageway.

The dispensing package 20 is constructed of a tubular material which forms a container body 22 having a single, continuous wall 24 for holding the fluent commodity 26. The package of the preferred embodiment is constructed from a Saran$^R$ material that is of sufficient gage to provide the valve action described above. Although the aforementioned material is employed, other suitable thermoplastic and semirigid substances are equally utilizable. The tubular package is provided with a radio-frequency welded bottom seal 28 and an engraved array 30 forming neck seal 32. For accuracy of description, the portion of the neck seal toward the bottom seal is nomenclated as the rearward portion 34 thereof and that opposite, the forward portion 36 thereof. The rearward neck seal portion 34 is constructed as to flatten the tubular body forming two opposed substantially flat members, 38, of semirigid material. The rearward portion 34 is discontinuously structured thereby forming a lead orifice 40 for providing a passageway from the inside of the container between members 38. Likewise, the forward portion 36 is discontinuously structured thereby forming a discharge orifice 42. Medial the orifices 40 and 42 is provided a formed valve 44 which, when actuated to the open position by applying pressure to the concave portion 46, FIG. 2, of formed valve 44, and discharge orifice 42. The details of construction of formed valve 44 are given below in the discussion of FIGS. 3 through 7. Depending upon the fluid being dispensed, the discharge orifice 42 may be so dimensioned so as to provide a stream of fluid or to break up the fluid flow into fine droplets thereby causing the package to be an aerosol dispenser.

Referring now to FIGS. 3 through 5, the detailed description of the formed valve 44 is provided. A depression 48 is formed in the upper member of valve 44. While in the preferred embodiment herein described the depression 48 is shown as a spheric section, it is understood that the depression could be formed from any smooth-curved section as, for example, ellipsoidal or parabaloidal, which provides a smooth-curved underside at the contact surface. Specifically, FIG. 4 shows a substantially flat member 38 which has a spherical depression. In FIG. 3, the upper or exterior surface 50 is constructed to be contiguous with the outer surface of continuous wall 24; and the lower or interior surface 52 thereof, with the interior surface of continuous wall 24. The lower surface 52 in its application through this invention becomes the contact or sealing surface for controlling fluid flow.

The sealing property has been found to be enhanced by smoothness and finish of the material of construction. While almost any thermosetting plastic or thermoplastic film or thin sheet has been found suitable, the use of radio-frequency welding techniques is most desirable. For this process, the plastics used have included, but not been limited to, acrylonitrile-butadiene-styrene, acrylonitrile-styrene-acrylic elastomer, acetals, acrylics, allyl resins and monomers, cellulosic molding compounds, epoxy resins, fluoroplastics, ionomers, melamine molding compounds, nylons, phenolic molding compounds, phenylenic molding compounds, polymeric plastic molding compounds, polyesters, polyethylenes, polypropylenes, polystyrenes, polymethans, vinyl polymers, and vinyl copolymers.

In forming the depression, the radius about tip 56 is set in such a manner that upon operation, the lip does not reverse to a position on the exterior surface 50 side of flat member 38, but allows the central portion 58 of the depression to operate to such a position.

The opposite flat member 38 in which is formed the corresponding impression 60 is shown in FIG. 4. Upper or interior surface 62 has impressed therein the same smooth-curved aspect as the depression 48. Dimensionally the height 64 of the convexity of depression 48 and the height 66 concavity of impression 60 match as closely as possible so as to nest and provide complete sealing when depression 48 is maximally extended in the direction from exterior surface 50 toward interior surface 52, when impression 60 is similarly extended, and when the two mating surfaces are placed in abutting relationship shown in FIG. 5. In the position shown, interior surfaced 52 and 62 contact one another and may for purposes of identification also be termed contacting surfaces.

The exterior surface 66 of impression 60 differs in its physical requirements from depression 48. This is particularly true with respect to lip 68 and central portion 70. In terms of analogy to valve technology, depression 48 serves as a gate or vane to arrest the flow of fluid 26. Similarly, impression 60 serves the dual role of a valve seat and a valve operator. Thus, while impression 60 needs to be flexible so as to perform as an operator, the central portion 70 need not remain at the operated position, but can return to a normal, at-rest, smooth-curved position. Lip 68 of impression 60 may optionally be constructed with the same set as described for lip 56. Also, extra material may be accumulated adjacent the perimeter 72 on exterior surface 66 to cause flexed central portion 70 to return to the at-rest condition.

While the above description applies to a self-contained valved package which is made from a single piece of tubular material, it is obvious to those who are skilled-in-the-art that a similar package could be made from two separate sheets being sealed around the perimeter, except for the opening to the valve thereof. In such a configuration, the valve could reasonably be placed at any location about the perimeter of the package.

The operation of the package is shown in FIGS. 6 and 7. FIG. 6 shows the operator depressing impression 60 of valve 44 so as to operate depression 48 from the smooth-curved position to the multiply curved position as shown in FIGS. 4 and 5. Upon operating the valve in this manner, the valve maintains its open condition, FIG. 5, until such time as the process of valve operation is reversed. FIG. 7 shows the expressing of the fluent commodity 26 from the package 20 by compressing the flexible side walls of the package. The use of pressure in this manner is completely dependent upon such factors as (1) viscosity of the fluent commodity; (2) the sizing of the orifices 40 and 42 at either side of the valve 44, and; (3) the geometry of the valve-seat relationship when operated to the open or multiply curved position.

It will of course be appreciated that the embodiments hereinbefore described have been given purely by way of illustration and example, and may be modified as to detail without thereby departing from the basic principles of the invention.

What is claimed is:

1. A dispensing package for a fluent commodity comprising
    a collapsible tube with a self-contained depression-/impression valve formed from two wall portions thereof (in the wall of said collapsible tube) operable between an open position and a closed position for discharging said commodity, (and) further comprising:
    a depression in the first one of said wall portions operable between a smooth-curved position and a multiply curved position;
    an impression in the second one of said wall portions which when said depression is in the smooth-curved position, mates with and seals against said depression for preventing discharge of said fluent commodity, and, which when said depression is in the multiply curved position said second one of said wall portions is operated to a multiply curved position forming at least one opening between the two opposed wall portions, for permitting discharge of said fluent commodity; and
    said wall is of a flexible material whereby upon said valve being operated to said open position, momentary pressing of said wall forces said commodity through said valve.

2. A dispensing package as in claim 1 wherein said collapsible tube is formed from a single length of tubular flexible material.

3. A dispensing package as in claim 2 wherein said flexible material is selected from a group consisting of acrylonitrile-butadiene-styrene, acrylonitrile-styrene-acrylic elastomer, acetals, acrylics, allyl resins and monomers, cellulosic molding compounds, epoxy resins, fluoroplastics, ionomers, melamine molding compounds, nylons, phenolic molding compounds, phenylenic molding compounds, polymeric plastic molding compounds, polyesters, polyethylenes, polypropylenes, polystyrenes, polymethanes, vinyl polymers, and vinyl copolymers.

4. A dispensing package for a fluent commodity comprising a container formed from a single length tubular flexible material
    an elongated discharge passage attached thereto having two opposed substantially flat wall portions;
    a depression in the first one of said wall portions operable between a smooth-curved position and a multiply curved position;
    an impression in the second one of said wall portions which when said depression is in the smooth-curved position, mates with and seals against said depression for preventing discharge of said fluent commodity, and, which when said depression is in the multiply curved position said second one of said wall portions is operated to a multiply curved position forming at least one opening between the two opposed wall portions, for permitting discharge of said fluent commodity; and
    whereby upon said valve being operated to said open position momentary pressing of said wall forces said commodity through said valve.

5. A dispensing package as in claim 4 wherein said flexible material is selected from a group consisting of acrylonitrile-butadiene-styrene, acrylonitrile-styrene-acrylic elastomer, acetals, acrylics, allyl resins and monomers, cellulosic molding compounds, epoxy resins, fluoroplastics, ionomers, melamine molding compounds, nylons, phenolic molding compounds, phenylenic molding compounds, polymeric plastic molding compounds, polyesters, polyethylenes, polypropylenes, polystyrenes, polymethanes, vinyl polymers, and vinyl copolymers.

6. A dispensing package as in claim 5 wherein said depression in the smooth-curved position is an ellipsodial section.

7. A dispensing package as in claim 6 wherein said ellipsodial section is a spheric section.

8. A dispensing package as in claim 5 wherein said depression in the smooth-curved position in a paraboloidal section.

9. A dispensing package as in claim 4 further comprising a depression having a unidirectional die-formed lip preventing operation to a smooth-curved position on both sides of said wall portion.

10. A dispensing package as in claim 6 wherein said impression is an ellipsodial section for mating with interior side of said depression.

11. A dispensing package as in claim 10 wherein said ellipsoidal section is a spheric section.

12. A dispensing package as in claim 10 wherein said impression is a paraboloidal section for mating with interior side of said depression.

* * * * *